United States Patent

Kanaoka et al.

Patent Number: 5,847,108
Date of Patent: Dec. 8, 1998

[54] CLATHRATE OF ISOFLAVONE DERIVATIVES AND EDIBLE COMPOSITION COMPRISING THE SAME

[75] Inventors: Satomi Kanaoka, Osaka; Takehiko Uesugi, Nishinomiya; Kuniaki Hirai, Akashi; Toshiya Toda, Nishinomiya; Takenori Okuhira, Kobe, all of Japan

[73] Assignee: Fujicco Co., Ltd., Hyogo, Japan

[21] Appl. No.: 820,605

[22] Filed: Mar. 19, 1997

[30] Foreign Application Priority Data

Mar. 21, 1996 [JP] Japan .................................. 8-064372

[51] Int. Cl.$^6$ .......................... C08B 37/16; A61K 31/715
[52] U.S. Cl. .............................................. 536/103; 514/58
[58] Field of Search ................. 536/103; 514/58

[56] References Cited

U.S. PATENT DOCUMENTS

| | | |
|---|---|---|
| 4,826,963 | 5/1989 | Stadler nee Szoke et al. ........ 536/103 |
| 5,043,326 | 8/1991 | Stadler nee Szoke et al. .......... 514/58 |
| 5,624,910 | 4/1997 | Vallee et al. ............................... 514/27 |

*Primary Examiner*—Douglas W. Robinson
*Assistant Examiner*—Everett White
*Attorney, Agent, or Firm*—Marshall, O'Toole, Gerstein, Murray & Borun

[57] ABSTRACT

Clathrate compounds comprising an isoflavone derivative and a cyclodextrin are disclosed. The clathrate compounds have improved water solubility and good taste properties, thereby making the compounds a useful ingredient in edible compositions.

3 Claims, 8 Drawing Sheets

CLATHRATE OF ISOFLAVONE DERIVATIVES AND EDIBLE COMPOSITION COMPRISING THE SAME

FIELD OF THE INVENTION

The present invention relates to a clathrate with cyclodextrin of isoflavone derivatives contained in soybean or fermented soybean (the Japanese food "natto"), and an edible composition comprising the clathrate. More particularly, the present invention relates to a clathrate of isoflavone derivatives wherein the bitterness, acerbity, and astringency originally expressed by the isoflavone derivatives are suppressed, and water solubility of the isoflavone derivatives is improved. Thus the isoflavone derivatives can be suitably utilized in edible compositions. Moreover, the functions in a living body by such isoflavone derivatives are improved through improvement of the absorption rate of the isoflavone derivatives into a human body.

BACKGROUND OF THE INVENTION

Isoflavone derivatives are one of the flavonoid glycosides contained in plants such as Glycine, etc. Physiological activities of the isoflavone derivatives are known in general, for example, estrogen actiin, antioxidative activity, and antimicrobial activity.

It is well known that the mortality of Japanese caused by breast cancer or prostate cancer is considerably lower than Western people. Epidemio-logical investigation has confirmed that the urinary excretion of daizin in Japanese female is ten times greater than that of a female in Boston or Helsinki, and that the isoflavone level in the blood of Japanese male is much higher than that of Finnish male, e.g., as high as 40 times. Accordingly, it has been reported that the mortality of Japanese caused by breast cancer or prostate cancer has been kept at a low level because the Japanese ingest a large amount of isoflavone derivatives. See, H. Adlercreutz, H. Honjo, A. Higashi, T. Fotsis, E. Hamalaimen, T. Hasegawa, and H. Okada, *Am. J. Clin. Nutr.*, 54, 1093(1991); H. Adlercreutz, H. Markkanen, and S. Watanabe, *Lancet,* 342, 1209 (1993). Consequently, carcinostatic actions by the isoflavone derivatives have been suggested.

Such a high isoflavone derivatives level in the urine or blood of Japanese people is presumed to result from the traditional Japanese habit of ingesting a large amount of soybeans or food made of, or from, soybeans.

Moreover, it was confirmed that isoflavone derivatives suppress a decrease in bone density in ovariectomized rats with low calcium diet. Thus, the isoflavone derivatives are considered as prophylactic compounds for osteoporosis. (See Japanese Patent Provisional Publication No. 7-36598.)

As mentioned above, isoflavone derivatives have various useful functions, and it is believed that administering the isoflavone derivatives would play an important role in maintaining and promoting healthy conditions.

Isoflavone derivatives are extracted from soybean or fermented soybean using a solvent, such as hot water, alcohol, or the like. Majority of the isoflavone derivatives so extracted are daidzin and genistin. Threshold values of daidzin, genistin, and glycitin are $10^{-2}$ mm, $10^{-1}$ mM, and $10^{-3}$ mM (millimolar), respectively. Threshold values for the malonylated form, acetylated form, or aglycon thereof tend to be even lower. (See, Kazuyoshi Okubo, Yumiko Yoshiki, Masaki Yoshikoshi, Chigen Tsukamoto, Shigemitsu Kudo, *New Food Industry*, 36 (1994).)

Besides having such low threshold values, i.e., bitterness, acerbity, and astringency, the isoflavone derivatives are slightly soluble in water. Therefore, the application of isoflavone derivatives in edible compositions has not been practiced because of such drawbacks.

In addition, during the preparation of processed foods that are made essentially from soybean, e.g., soymilk, tofu (soybean curd), and the like, such isoflavone derivatives, which are effective in maintaining healthy conditions as above described, often have been intentionally removed in order to avoid the characteristic taste of the isoflavone derivatives.

Furthermore, because the low water solubility of the isoflavone derivatives leads to a low absorption rate into human body, sufficient beneficial effects thereof cannot be achieved unless a large amount of the derivatives are administered.

SUMMARY OF THE INVENTION

As stated above, although the isoflavone derivatives have remarkable effects, they have not been utilized in edible compositions because of the sensory problems and the low water solubility.

The object of the present invention is to enable the positive application of isoflavone derivatives in edible compositions, and to improve physiological actions in the living body by raising the absorption rate into the body, by suppressing the bitterness, acerbity, and astringency thereof, and by improving the water solubility of the isoflavone derivatives.

The inventors made strenuous efforts and accomplished the present invention through finding that the bitterness, acerbity, and astringency attributed to the isoflavone derivatives can be suppressed, and the water solubility thereof can be improved, by clathrating the isoflavone derivatives with cyclodextrins.

Thus, the present invention is directed to a clathrate of isoflavone derivatives, wherein said isoflavone derivatives are clathrated with a β-cyclodextrin, a γ-cyclodextrin, or a mixture thereof.

DETAILED DESCRIPTION OF THE PREFERRED EMBODIMENTS

Fifteen compounds have been found and identified heretofore as isoflavone derivatives contained in soybean and natto (i.e., fermented soybean). Each of these isoflavone derivatives has bitter, acerb, and astringent taste. In addition, an irritating feeling temporarily develops in the throat after the isoflavone derivatives are taken orally.

The name and structure of each of the fifteen isoflavone derivatives are listed in Table 1 and Table 2 with reference to the general formulae (I) and (II), respectively.

TABLE 1

| Isoflavone Derivatives Having the General Formula [I] | $R^1$ | $R^2$ | $R^3$ |
|---|---|---|---|
| 1. daidzin | H | H | H |
| 2. glycitin | H | $OCH_3$ | H |
| 3. genistin | H | H | OH |
| 4. 6"-O-acetyldaidzin | $COCH_3$ | H | H |
| 5. 6"-O-acetylglycitin | $COCH_3$ | $OCH_3$ | H |
| 6. 6"-O-acetylgenistin | $COCH_3$ | H | OH |
| 7. 6"-O-malonyldaidzin | $COCH_2COOH$ | H | H |
| 8. 6"-O-malonylglycitin | $COCH_2COOH$ | $OCH_3$ | H |
| 9. 6"-O-malonylgenistin | $COCH_2COOH$ | H | OH |
| 10. 6"-O-succinyldaidzin | $COCH_2CH_2COOH$ | H | H |
| 11. 6"-O-succinylglycitin | $COCH_2CH_2COOH$ | $OCH_3$ | H |
| 12. 6"-O-succinylgenistin | $COCH_2CH_2COOH$ | H | OH |

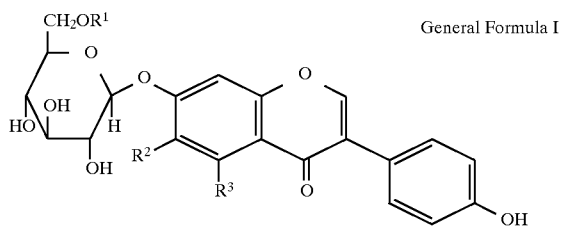

General Formula I

TABLE 2

| Isoflavone Derivatives Having the General Formula [II] | $R^4$ | $R^5$ |
|---|---|---|
| 13. daidzein | H | H |
| 14. glycitein | H | $OCH_3$ |
| 15. genistein | OH | H |

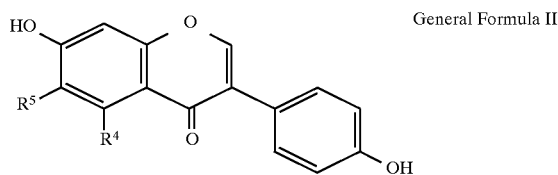

General Formula II

The isoflavone derivatives suitably used in the present invention are selected from the group consisting of daidzein, genistein, glycitein, daidzin, genistin, glycitin, 6"-O-malonyldaidzin, 6"-O-malonylgenistin, 6"-O-malonylglycitin, 6"-O-acetyldaidzin, 6"-O-acetylgenistin, 6"-O-acetylglycitin, 6"-O-succinyldaidzin, 6"-O-succinylgenistin, 6"-O-succinylglycitin, and mixtures thereof. The isoflavone derivatives are obtained by extraction from soybean or natto using a solvent, such as hot water, alcohol or the like, followed by a suitable purification procedure. However, the majority of the isoflavone derivatives contained in such an extract are daidzin and genistin.

Figure 1:
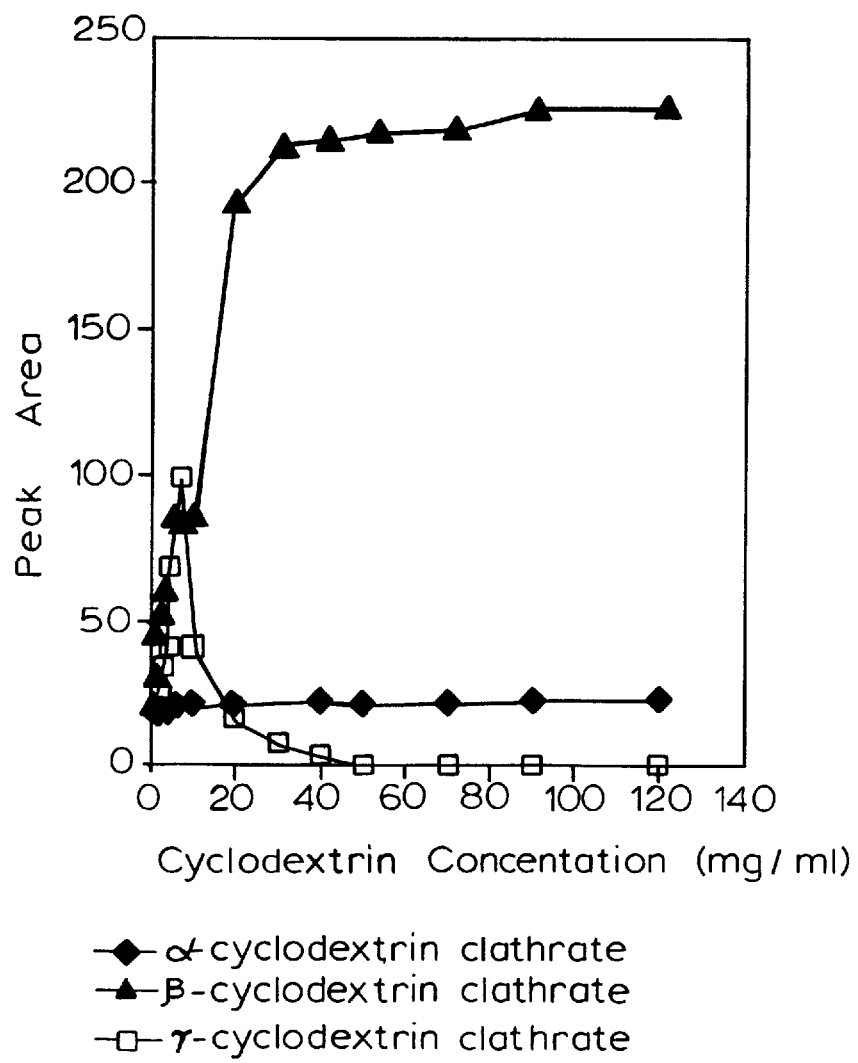
FIG. 1 is a graph illustrating formation of the clathrate of daidzin with various cyclodextrins.
Figure 2:
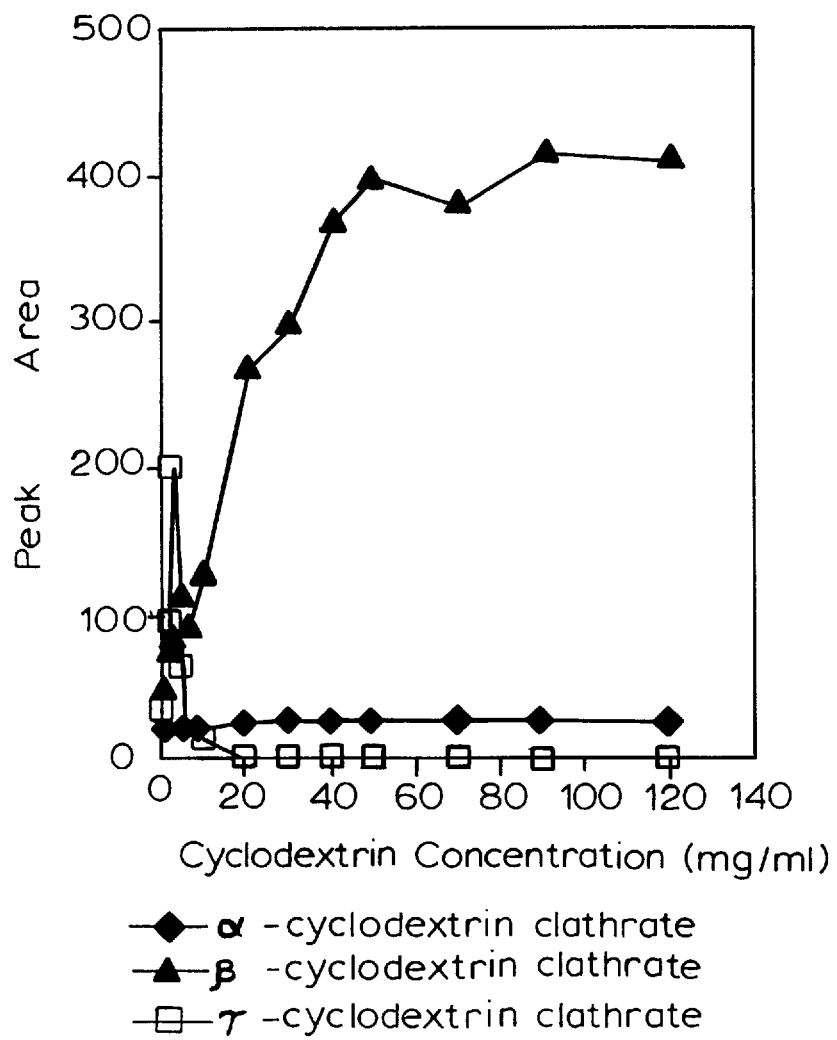
FIG. 2 is a graph illustrating formation of the clathrate of genistin with various cyclodextrins.
Figure 3:
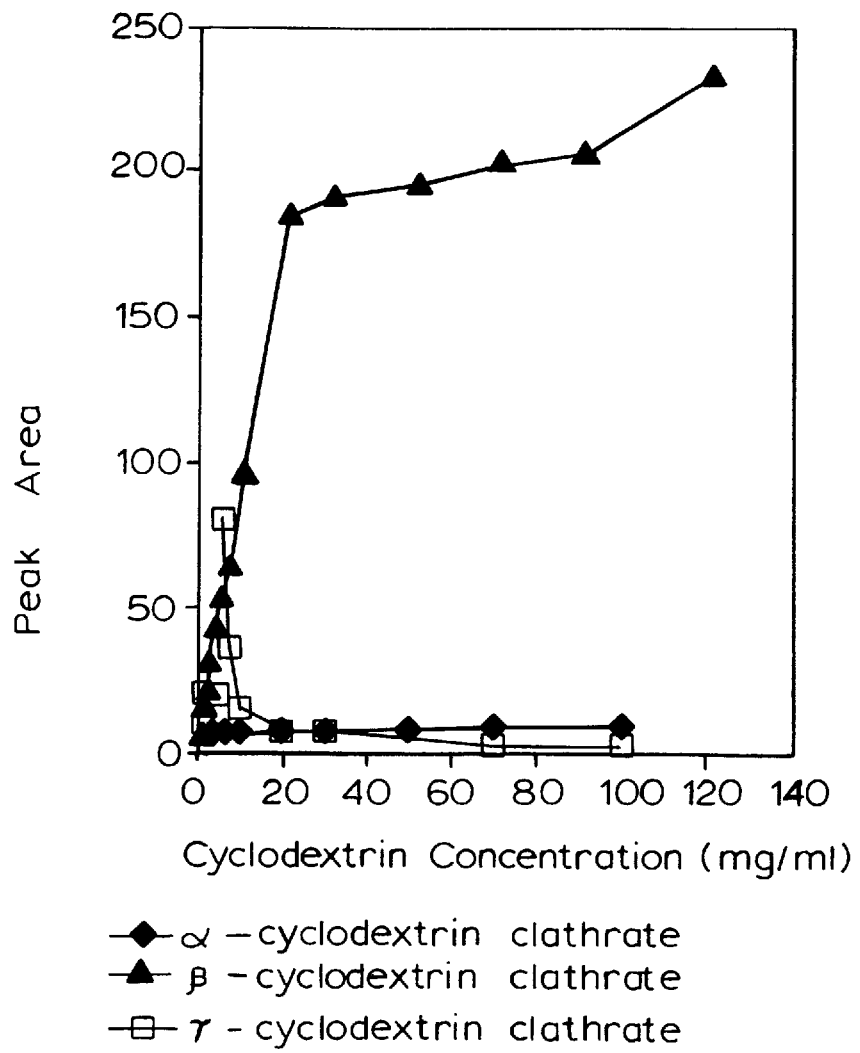
FIG. 3 is a graph illustrating formation of the clathrate of daidzein with various cyclodextrins.
Figure 4:
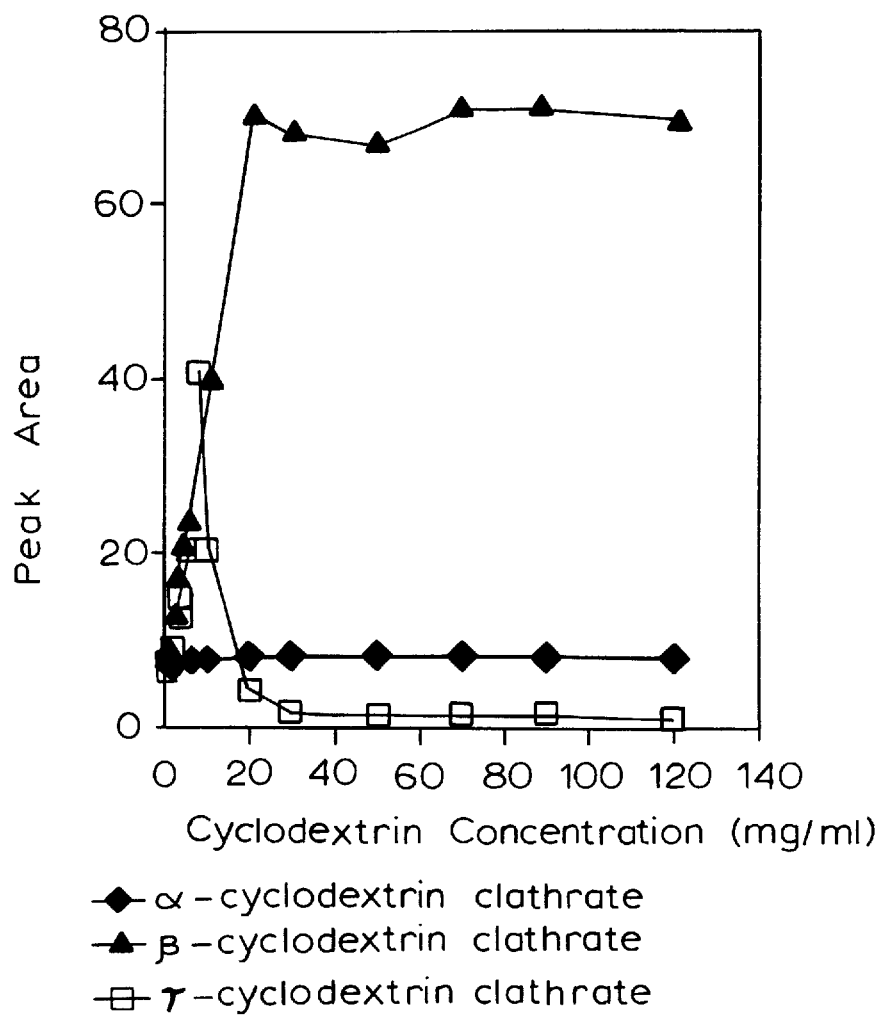
FIG. 4 is a graph illustrating formation of the clathrate of genistein with various cyclodextrins.
Figure 5:
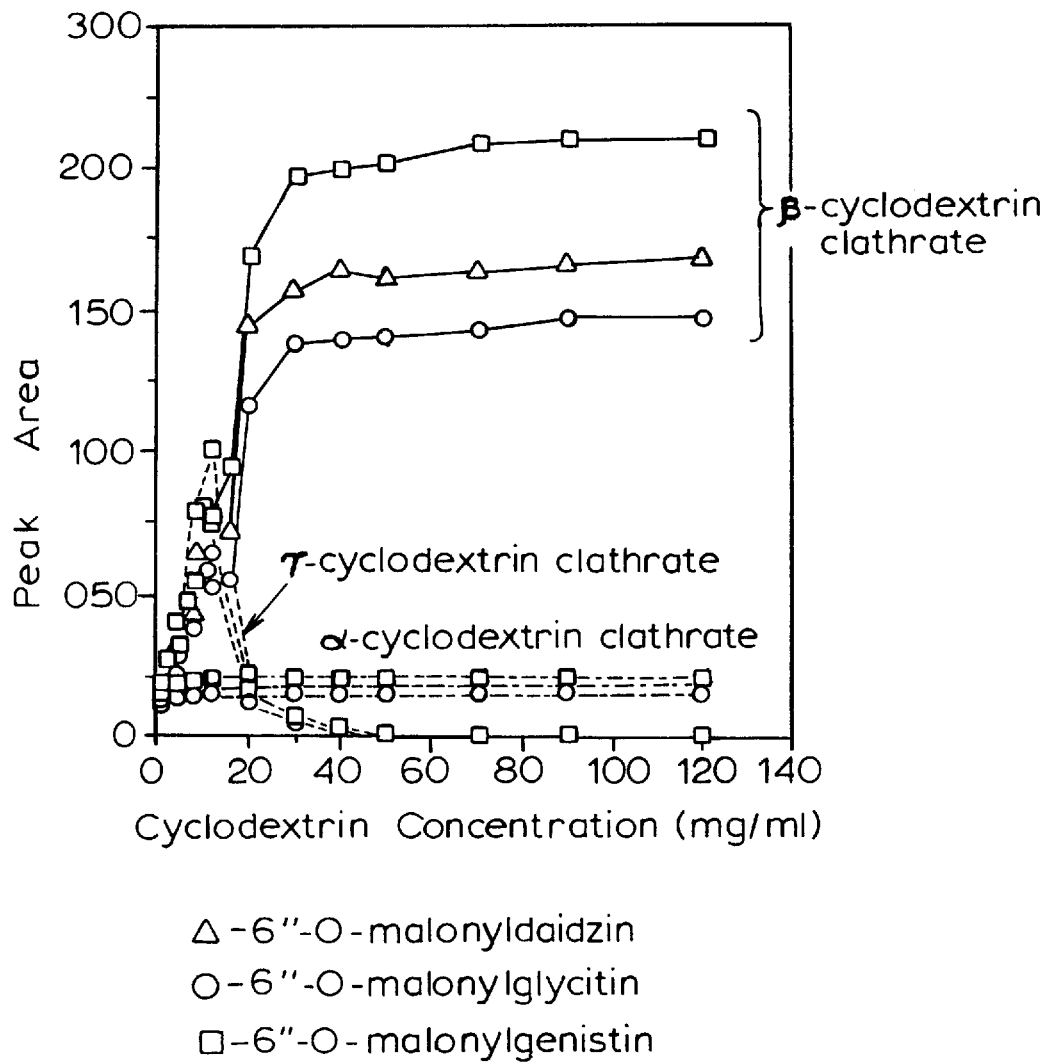
FIG. 5 is a graph illustrating formation of the clathrate of 6"-O-malonyldaidzin, 6"-O-malonylgenistin, and 6"-O-malonylglycitin with various cyclodextrins.
Figure 6:
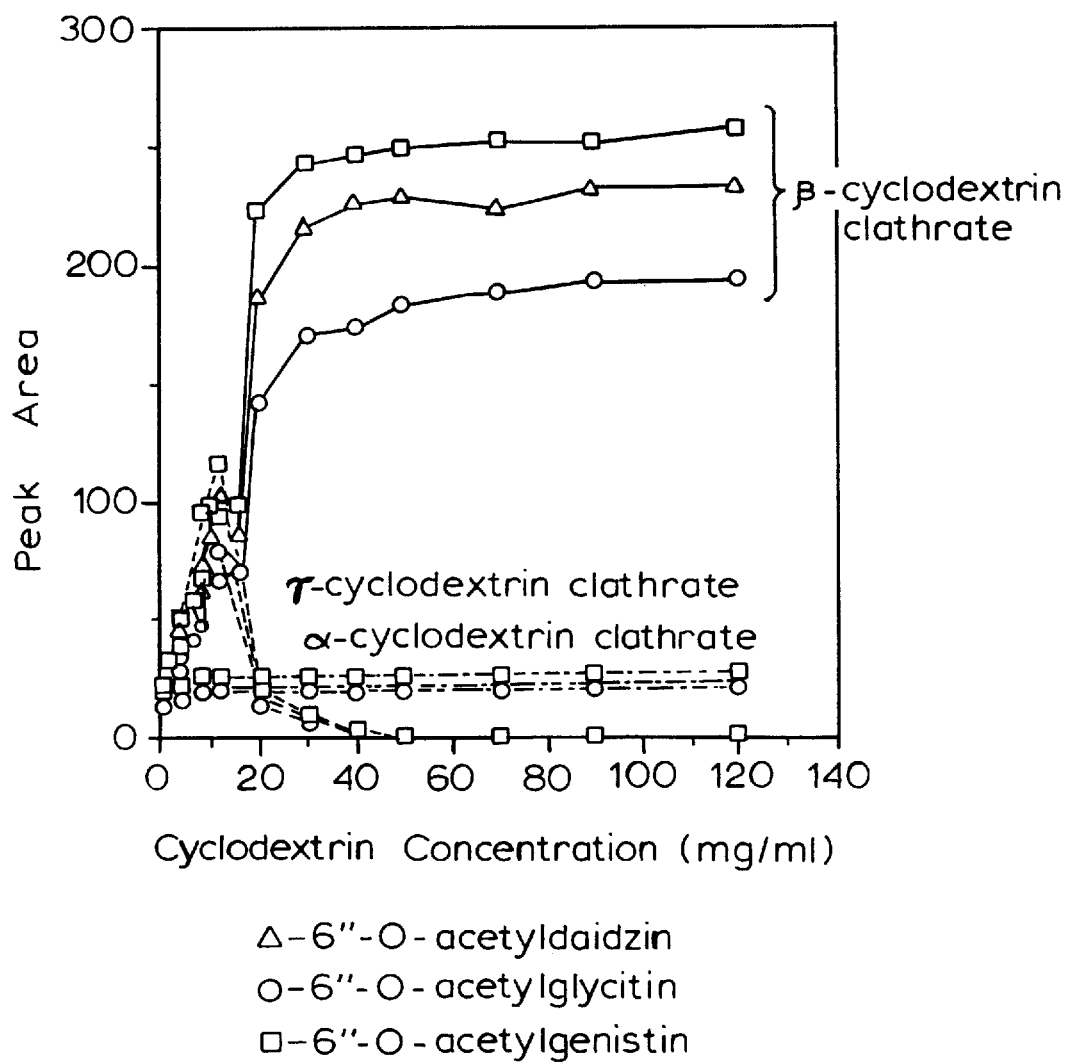
FIG. 6 is a graph illustrating formation of the clathrate of 6"-O-acetyldaidzin, 6"-O-acetylgenistin, and 6"-O-acetylglycitin with various cyclodextrins.
Figure 7:
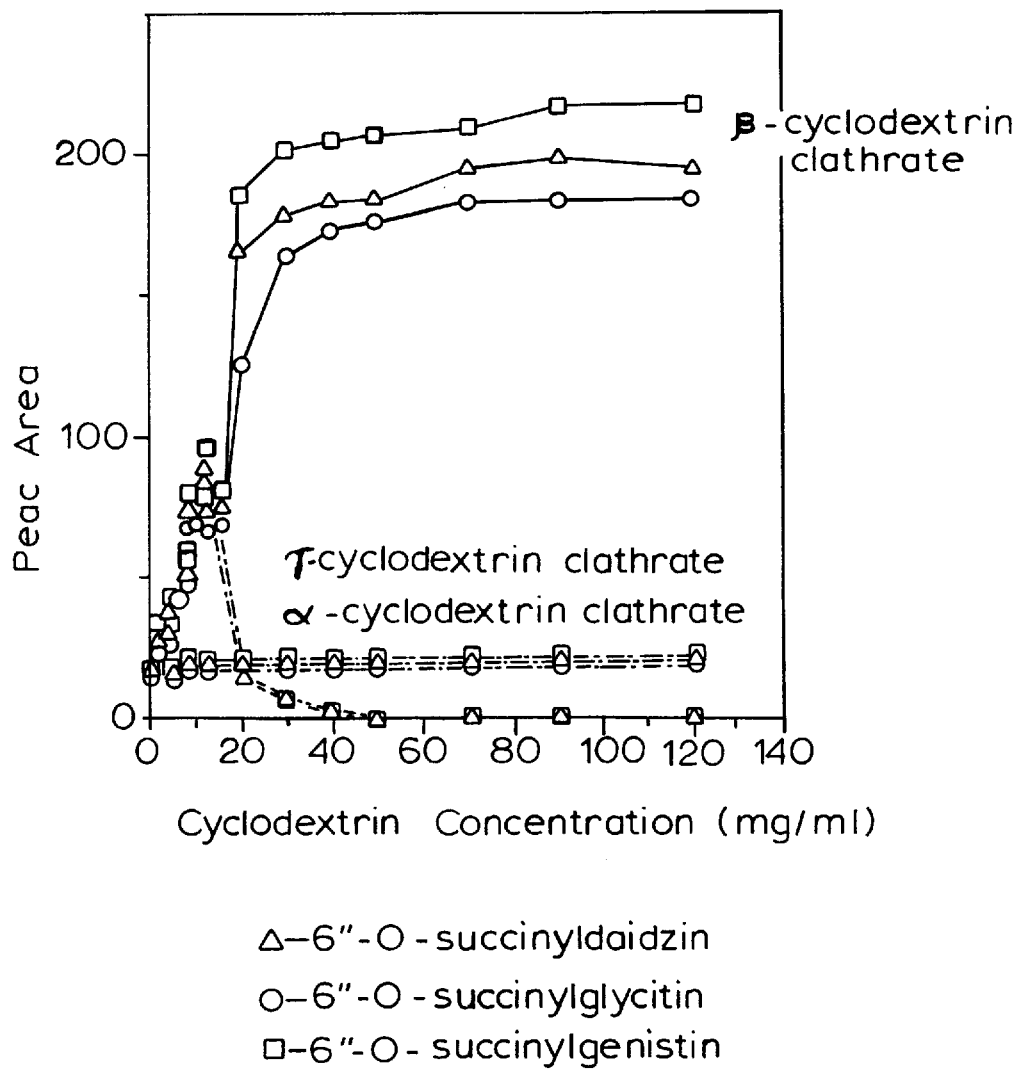
FIG. 7 is a graph illustrating formation of the clathrate of 6"-O-succinyldaidzin, 6"-O-succinylgenistin, and 6"-O-succinylglycitin with various cyclodextrins.
Figure 8:
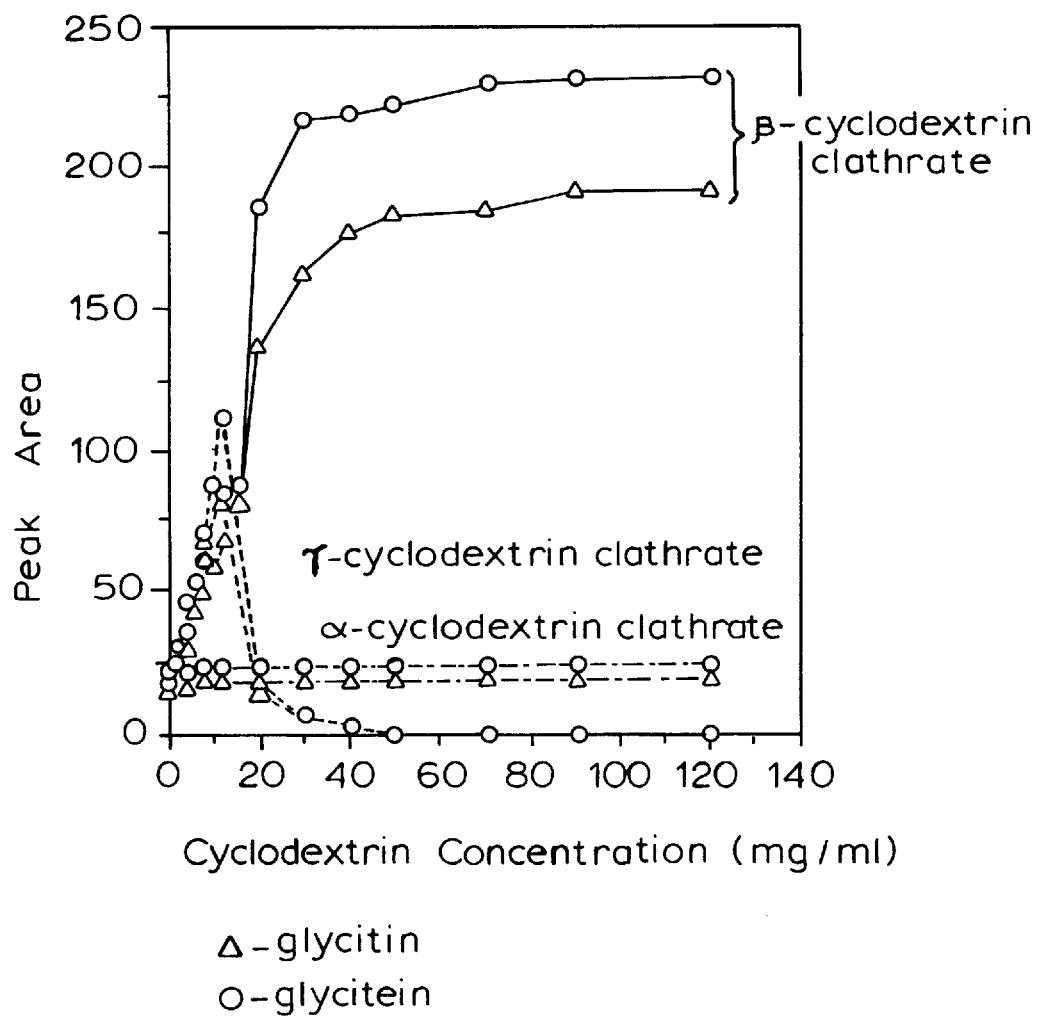
FIG. 8 is a graph illustrating formation of the clathrate of glycitin and glycitein with various cyclodextrins.

Meanwhile, cyclodextrins are nonreducing maltoligosaccharides, in which 6 to 12 glucose molecules are annularly linked via α-1,4 glucoside bonds, and are prepared by a reaction of starch with cyclodextrin glucan- otransferase (CGTase) from *Bacillus macerans* and the like. Known general cyclodextrins include α-cyclodextrin consisting of six molecules of glucose, β-cyclodextrin consisting of seven molecules of glucose, and γ-cyclodextrin consisting of eight molecules of glucose. In a preferred embodiment of the present invention, β-cyclodextrin or γ-cyclodextrin is considered to be a suitable partner of the isoflavone derivatives. In particular, these cyclodextrins are especially well clathrated with the isoflavone derivatives to provide the desired effects (see FIGS. 1 to 8).

These cyclodextrins can be used alone or in combination. Moreover, clathrating with a branched or methylated β-cyclodextrin or γ-cyclodextrin having improved solubility can also be effective.

Methods of making the clathrate of the above isoflavone derivatives with the above cyclodextrins are described below.

There are various methods for making a clathrate of isoflavone derivatives with cyclodextrins. A representative method is kneading. That is to say, water is added to a cyclodextrin in an amount of about 0.1 to 6 weight by parts of the cyclodextrin, then the mixture is well kneaded to become pasty in form, and finally the isoflavone derivatives are added thereto followed by sufficient kneading. The dry weight ratio of the isoflavone derivatives to the cyclodextrins can be between 1:0.1 and 1:50, and preferably, between 1:3 and 1:10. The kneading time can be from about 30 minutes to 3 hours. A kneader mixer, ball mill, emulsifier, and the like, can be used as the kneading device. The paste can be spray dried, dried under reduced pressure, or dried by a drum method after clathration.

In a clathrate of the isoflavone derivatives thus obtained, the bitterness, acerbity, and astringency of the original isoflavone derivatives were suppressed, and water solubility of the clathrate also was improved. Accordingly, the clathrates are extremely suitable for application in edible compositions, and can improve the absorption rate into the body to enhance the physiological activity thereof.

A clathrate of the isoflavone derivatives of the present invention can be mixed in an edible composition to be ingested. The ingestion dose of the clathrate can be varied in accordance with the condition, age, or the like, of the recipient subject. Usually, 0.1 to 4 mg/kg body weight/day, preferably, 0.2 to 1 mg/kg body weight/day of the isoflavone derivatives dosage is employed. Ingestion can be once per day, or otherwise, can be divided into multiple doses if necessary.

The edible composition can be of any form, for example, a beverage, a confectionery, processed foods, seasonings, or the like, without any limitation. In order to prepare the edible composition, the ingredients, such as excipient, filler, stabilizer, emulsifier, sweetener, flavor, colorant, color fixative, and the like, each of which is commonly employed in the art, can be suitably mixed, as long as they do not exert undesirable effects on the active component of the edible composition of the present invention.

Nonlimiting examples of the present invention are described below to explain the present invention in more detail.

EXAMPLE

Clathrate Formation Test

First, various clathrates were prepared through clathration of several isoflavone derivatives with several cyclodextrins, and the following experiments were carried out to determine water solubility of each clathrate.

Ten milligrams (mg) of each of fifteen isoflavone derivatives, i.e., daidzin (FIG. 1); genistin (FIG. 2); daidzein (FIG. 3); genistein (FIG. 4); 6"-O-malonyldaidzin, 6"-O-malonylgenistin, and 6"-O-malonylglycitin (FIG. 5); 6"-O-acetyldaidzin, 6"-O-acetylgenistin, and 6"-O-acetylglycitin (FIG. 6); 6"-O-succinyldaidzin, 6"-O-succinylgenistin, and 6"-O-succinylglycitin (FIG. 7); and glycitin and glycitein (FIG. 8) were placed in individual test tubes, respectively, with α-, β-, or γ-cyclodextrin in an amount shown in FIGS. 1 through 8 (i.e., 0 to 1.2 grams (g)) together with 10 milliliter (ml) of distilled water, then mixed with stirring overnight at room temperature. Next, each solution was filtered through a glass filter and the filtrate was analyzed using high performance liquid chromatography. High performance liquid chromatography was performed using an SC-8020 (Toso, JAPAN) equipped with a column YMC pack ODS-AM-303 (φ4.6×200 millimeters (mm), YMC, JAPAN). The solvent system for analysis was a linear gradient from 15% acetonitrile/0.1%acetic acid aqueous solution to 35% acetonitrile/0.1% acetic acid aqueous solution at flow rate 1.0 ml/min, and absorption at 254 nanometers (nm) was detected to determine peak areas of the isoflavone derivatives. The results are shown in FIGS. 1 through 8.

The isoflavone derivatives employed were clathrated with each of the cyclodextrins to form the clathrates. The increase in formation of the clathrate has been shown in FIGS. 1 through 8, based on the increase in peak areas of respective isoflavone derivatives. Pattern of variation in solubility of respective isoflavone derivatives are similar, and the highest level of clathrate was yielded when β-cyclodextrin was used as a partner, thereby suggesting that best improvement in solubility was accomplished with β-cyclodextrin.

Thereafter, the absorption rate in the body and physiological activity of those clathrates of the isoflavone derivatives were examined.

EXAMPLE 1

Comparison of Absorption Rate and Physiological Activity of β-cyclodextrin Clathrates with Various Isoflavone Derivatives To obtain postmenopausal osteoporosis model, eighty-day-old Sprague-Dawley rats, on day 10 after ovariectomy, was grown for 28 days feeding with calcium deficient diet (Ca: 0.004%, P: 0.3%), with one group consisting of 5 to 6 rats. During the time the rats were growing, an isoflavone derivative, or a β-cyclodextrin clathrate thereof (see Table 3), was administered orally in the form of a solution or a suspension in 1% aqueous hydroxypropylcellulose. On the day before the final administration, urine was collected for 24 hours. Blood was collected from postcava at 4 hours after the final administration, and a femur was removed. The collected blood was separated to obtain serum according to a standard method. In order to determine the amounts of isoflavone derivatives in the obtained samples of urine and serum, the samples were subjected to the reactions for 2 hours at 37° C. through adding thereto 50 Units/ml of sulfatase (EC3.1.6.1; SIGMA CHEMICAL Co. LTD.) in 1 ml of acetate buffer (0.1M, pH 4.5). Then 1 ml of acetate buffer (0.1M, pH 4.5) containing β-glucuronidase (200 Units/ml, EC 3.2.1.31, WAKO JYUNYAKU KOGYO KABUSIKI KAISYA) was added to the mixture and incubated for 2 hours at 37° C. After treating it with Sep-Pak (Waters), the incubated solution was analyzed using HPLC as described in the above clathrate formation test. Concentration of each isoflavone derivatives in the sample was determined based on the values for daidzein, genistein, or glycitein as a standard. Bone density of femur was calculated based on wet weight and volume measured by pycnometer. The results are shown in the Table 3 below.

TABLE 3

| | Blood Level Meaas ± S.D. (mg/ml) | Urinary Excretion Rate Means ± S.D. (%) | Bone Density Means ± S.D. (g/ml) |
|---|---|---|---|
| control | | | 1.457 ± 0.012 |
| daidzin | 0.84 ± 0.03 | 9.3 ± 0.7 | 1.496 ± 0.015 b |
| diadzin β-cyclodextrin clathrate | 8.92 ± 0.08 a | 18.3 ± 1.5 a | 1.532 ± 0.014 a, b |
| genistin | 0.78 ± 0.04 | 9.2 ± 0.5 | 1.502 ± 0.007 b |
| genistin β-cyclodextrin clathrate | 8.34 ± 0.12 a | 16.2 ± 1.6 a | 1.534 ± 0.012 a, b |
| glycitin | 0.75 ± 0.06 | 8.6 ± 0.6 | 1.494 ± 0.015 b |
| glycitin β-cyclodextrin clathrate | 7.82 ± 0.14 a | 17.3 ± 1.2 a | 1.533 ± 0.011 a, b |
| daidzein | 0.65 ± 0.04 | 8.7 ± 0.6 | 1.489 ± 0.013 b |
| daidzein β-cyclodextrin clathrate | 6.98 ± 0.12 a | 16.9 ± 0.3 a | 1.542 ± 0.010 a, b |
| genistein | 0.68 ± 0.03 | 9.1 ± 0.8 | 1.492 ± 0.012 b |
| genistein β-cyclodextrin clathrate | 7.24 ± 0.09 a | 16.2 ± 2.4 a | 1.546 ± 0.011 a, b |
| glycitein | 0.63 ± 0.05 | 8.2 ± 0.7 | 1.493 ± 0.013 b |
| glycitein β-cyclodextrin clathrate | 7.56 ± 0.14 a | 15.5 ± 2.6 a | 1.543 ± 0.015 a, b |
| 6"-O-malonyldaidzin | 0.85 ± 0.05 | 11.7 ± 1.2 | 1.488 ± 0.012 b |
| 6"-O-malonyldaidzin β-cyclodextrin clathrate | 8.95 ± 0.18 a | 19.8 ± 3.1 a | 1.544 ± 0.014 a, b |
| 6"-O-malonylgenistin | 0.84 ± 0.04 | 11.3 ± 2.1 | 1.494 ± 0.013 b |
| 6"-O-malonylgenistin β-cyclodextrin clathrate | 8.56 ± 0.12 a | 20.6 ± 2.8 a | 1.549 ± 0.012 a, b |
| 6"-O-malonylglycitin | 0.78 ± 0.05 | 10.4 ± 1.9 | 1.489 ± 0.012 b |
| 6"-O-malonylglycitin β-cyclodextrin clathrate | 8.23 ± 0.12 a | 19.3 ± 2.4 a | 1.539 ± 0.013 a, b |
| 6"-O-acetyldaidzin | 0.74 ± 0.05 | 10.4 ± 1.6 | 1.492 ± 0.014 b |
| 6"-O-acetyldaidzin β-cyclodextrin clathrate | 8.23 ± 0.12 a | 40.9 ± 1.9 a | 1.548 ± 0.023 a, b |
| 6"-O-acetylgenistin | 0.78 ± 0.07 | 11.2 ± 1.3 | 1.494 ± 0.028 b |
| 6"-O-acetylgenistin β-cyclodextrin clathrate | 8.67 ± 0.13 a | 20.6 ± 2.4 a | 1.538 ± 0.027 a, b |
| 6"-O-acetylglycitin | 0.72 ± 0.06 | 10.4 ± 0.9 | 1.489 ± 0.012 b |
| 6"-O-acetylglycitin β-cyclodextrin clathrate | 8.43 ± 0.09 a | 21.5 ± 2.8 a | 1.537 ± 0.019 a, b |
| 6"-O-succinyldaidzin | 0.86 ± 0.03 | 11.7 ± 1.8 | 1.490 ± 0.030 b |
| 6"-O-succinyldaidzin β-cyclodextrin clathrate | 6.88 ± 0.11 a | 22.1 ± 2.9 a | 1.546 ± 0.032 a, b |
| 6"-O-succinylgenistin | 0.82 ± 0.05 | 10.9 ± 1.9 | 1.486 ± 0.028 b |
| 6"-O-succinylgenistin β-cyclodextrin clathrate | 8.78 ± 0.12 a | 20.9 ± 1.8 a | 1.543 ± 0.031 a, b |

TABLE 3-continued

|  | Blood Level<br>Meaas ± S.D. (mg/ml) | Urinary Excretion Rate<br>Means ± S.D. (%) | Bone Density<br>Means ± S.D. (g/ml) |
|---|---|---|---|
| 6"-O-succinylglycitin | 0.79 ± 0.03 | 11.2 ± 0.9 | 1.477 ± 0.032 b |
| 6"-O-succinylglycitin β-cyclodextrin clathrate | 8.24 ± 0.12 a | 21.4 ± 1.9 a | 1.518 ± 0.042 a, b | a: significantly different from the value for the corresponding isoflavone derivatives not clathrated (level of significance: 1%)
b: significantly different from the value for the control group (level of significance: 1%)

From the results above, each concentration of the isoflavone derivatives in serum samples from the animals, at 4 hours after administering the β-cyclodextrin clathrate of the isoflavone derivatives, proved to be about 8 to 12 times higher than the samples from the animals administered nonclathrated isoflavone derivatives. Further, the urinary excretion level also was raised about two-fold. Therefore, clathration of the isoflavone derivatives with cyclodextrins resulted in elevation of the absorption efficiency thereof in a living body. Moreover, in comparison with the control group, bone density of the femur was increased in both groups, i.e., administered with clathrated and nonclathrated isoflavone derivatives. Thus, potential applicability to prophylaxis or treatment of osteoporosis with isoflavone derivatives was indicated, and such effect proved to be more potent in the group administered the clathrate of the isoflavone derivatives with cyclodextrins.

The clathrate of the present invention was prepared and applicability to the edible compositions thereof was studied as described below.

EXAMPLE 2

β-cyclodextrin Clathrate of Daidzin

Daidzin (2.0 g) was dissolved in 300 ml of 50% ethanol at 80° C. with 10 g of β-cyclodextrin. The solution was mixed with stirring for 2 hours, keeping the temperature about 60°–80° C. After the mixture was left standing at room temperature overnight, it was dried under reduced pressure to yield 11.8 g of a powder. The resulting β-cyclodextrin clathrate was evaluated by a panel of ten for bitterness, astringency, and roughness.

EXAMPLE 3

γ-cyclodextrin Clathrate of Daidzin

The similar process as described in Example 2 was carried out except that γ-cyclodextrin was used instead of β-cyclodextrin to obtain γ-cyclodextrin clathrate. The resulting γ-cyclodextrin clathrate was similarly evaluated by a panel of ten for bitterness, astringency, and roughness.

COMPARATIVE EXAMPLE 1

α-cyclodextrin Clathrate of Daidzin

The similar process as described in Example 2 was carried out except that α-cyclodextrin was used instead of β-cyclodextrin to obtain α-cyclodextrin clathrate. The resulting α-cyclodextrin clathrate was similarly evaluated by a panel of ten for bitterness, astringency, and roughness.

COMPARATIVE EXAMPLE 2

Daidzin

Daidzin was evaluated by a panel of ten for bitterness, astringency, and roughness.

The results of the evaluation referred to in the Example 2 through Comparative Example 2 are shown in Table 4 below.

TABLE 4

|  | Clathrate | Bitterness | Astringency | Roughness |
|---|---|---|---|---|
| Example 2 | β-cyclodextrin | − | − | − |
| Example 3 | γ-cyclodextrin | + | + | + |
| Comparative Example 1 | α-cyclodextrin | +++ | +++ | +++ |
| Comparative Example 2 | − | ++++ | ++++ | ++++ |

−: none
+: slight
++: middle
+++: strong
++++: very strong

From the results shown in Table 4 above, it is evident that the bitterness, astringency, and roughness of daidzin are suppressed when the isoflavone flavone derivatives are clathrated with β-cyclodextrin or γ-cyclodextrin. Further, it is demonstrated that suppression of the bitterness, astringency, and roughness of daidzin is more pronounced when the isoflavone derivatives are clathrated with β-cyclodextrin.

EXAMPLE 4

Clathrate of Isoflavone Derivatives with α-, β-, or γ-cyclodextrin

The similar process as described in Examples 2 and 3 and Comparative Example 1 was carried out to obtain clathrates of various isoflavone derivatives with α-, β-, or γ-cyclodextrin. The resulting clathrates were evaluated by a panel of ten for bitterness, astringency, and roughness. The results of the evaluation are shown in Table 5 below.

TABLE 5

| Isoflavone Derivatives | Clathrate | Bitterness | Astringency | Roughness |
|---|---|---|---|---|
| glycitin | β-cyclodextrin | − | − | − |
|  | γ-cyclodextrin | + | + | + |
|  | α-cyclodextrin | +++ | +++ | +++ |
| genistin | β-cyclodextrin | − | − | − |
|  | γ-cyclodextrin | + | + | + |
|  | α-cyclodextrin | +++ | +++ | +++ |
| 6"-O-acetyldaidzin | β-cyclodextrin | − | − | − |
|  | γ-cyclodextrin | + | + | + |
|  | α-cyclodextrin | +++ | +++ | +++ |
| 6"-O-acetylglycitin | β-cyclodextrin | − | − | − |
|  | γ-cyclodextrin | + | + | + |
|  | α-cyclodextrin | +++ | +++ | +++ |

TABLE 5-continued

| Isoflavone Derivatives | Clathrate | Bitterness | Astringency | Roughness |
|---|---|---|---|---|
| 6"-O-acetylgenistin | β-cyclodextrin | – | – | – |
|  | γ-cyclodextrin | + | + | + |
|  | α-cyclodextrin | +++ | +++ | +++ |
| 6"-O-malonyldaidzin | β-cyclodextrin | – | – | – |
|  | γ-cyclodextrin | + | + | + |
|  | α-cyclodextrin | +++ | +++ | +++ |
| 6"-O-malonylglycitin | β-cyclodextrin | – | – | – |
|  | γ-cyclodextrin | + | + | + |
|  | α-cyclodextrin | +++ | +++ | +++ |
| 6"-O-malonylgenistin | β-cyclodextrin | – | – | – |
|  | γ-cyclodextrin | + | + | + |
|  | α-cyclodextrin | +++ | +++ | +++ |
| 6"-O-succinyldiadzin | β-cyclodextrin | – | – | – |
|  | γ-cyclodextrin | + | + | + |
|  | α-cyclodextrin | +++ | +++ | +++ |
| 6"-O-succinylglycitin | β-cyclodextrin | – | – | – |
|  | γ-cyclodextrin | + | + | + |
|  | α-cyclodextrin | +++ | +++ | +++ |
| 6"-O-succinylgenistin | β-cyclodextrin | – | – | – |
|  | γ-cyclodextrin | + | + | + |
|  | α-cyclodextrin | +++ | +++ | +++ |
| daidzein | β-cyclodextrin | – | – | – |
|  | γ-cyclodextrin | + | + | + |
|  | α-cyclodextrin | +++ | +++ | +++ |
| glycitein | β-cyclodextrin | – | – | – |
|  | γ-cyclodextrin | + | + | + |
|  | α-cyclodextrin | +++ | +++ | +++ |
| genistein | β-cyclodextrin | – | – | – |
|  | γ-cyclodextrin | + | + | + |
|  | α-cyclodextrin | +++ | +++ | +++ |

–: none
+: slight
++: middle
+++: strong
++++: very strong

As is clear from Table 5, the bitterness, astringency, and roughness of all isoflavone derivatives are suppressed when they were clathrated with β-or γ-cyclodextrin.

EXAMPLE 5

Beverage Containing the Cyclodextrin Clathrate of Isoflavone Derivative

One hundred and twenty mg of the daidzin clathrated with β-cyclodextrin as described in Example 2 was dissolved in 90 ml of water. Nine grams of fruit juice, 5 g of granulated sugar, 0.5 g of citric acid, and 0.1 g of flavor were added thereto, then mixed with stirring. The mixture was successively sterilized for an instant at 122°–138° C., and bottled in a 100 cc glass bottle to make beverage containing the clathrate of daidzin. The resulting beverage was evaluated by a panel of ten for bitterness, astringency, and roughness.

COMPARATIVE EXAMPLE 3

Beverage Containing Isoflavone Derivative

A process similar to Example 5 was carried out except that 20 mg of daidzin powder was used instead of the clathrate described in Example 2 to prepare beverage containing daidzin. The resulting beverage was evaluated by a panel of ten for bitterness, astringency, and roughness.

The results of the evaluation referred to in the Example 5 and Comparative Example 3 are shown in Table 6 below.

TABLE 6

|  | Clathrate | Bitterness | Astringency | Roughness |
|---|---|---|---|---|
| Example 5 | β-cyclodextrin | – | – | – |
| Comparative Example 3 | – | ++++ | ++++ | ++++ |

–: none
+: slight
++: middle
+++: strong
++++: very strong

It is apparent from Table 6 that the beverage containing powdered daidzin was bitter, astringent, and rough (Comparative Example 3), wherein the beverage containing clathrated daidzin with β-cyclodextrin was not bitter, astringent, or rough at all (Example 5). Moreover, a precipitate was found immediately subsequent to completion of preparing the beverage according to Comparative Example 3. On the contrary, no precipitate was found subsequent to preparation of the beverage according to Example 4, even after 3 months storage. It was, therefore, concluded that higher water solubility is achieved when the isoflavone derivatives were clathrated.

EXAMPLE 6

Cookies Containing the Cyclodextrin Clathrate of Isoflavone Derivative

Eighty grams of butter and 0.1 g of salt were mixed to be creamy using a whip mixer, then 40 g of confectioner's sugar was added and ground with rubbing. After an egg which had been broken and beaten was added thereto, the resulting mixture was mixed. Then, sift flour (100 g) including 480 mg of the clathrate of daidzin with β-cyclodextrin (see Example 2) also was added and mixed. Thereafter, the resulting dough was rolled to a 4 mm thickness using a roller, then cut with a dough cutter, baked for 12 to 13 minutes at approximately 160° C. to 170° C. in an oven.

The resulting cookies were neither bitter nor astringent, and had a very good taste.

EXAMPLE 7

Clathrate of Crude Isoflavone Derivatives with β-cyclodextrin

Twenty ml of water was added to 10.0 g of β-cyclodextrin, and the mixture was kneaded for 30 minutes to provide a paste. Then, 2.0 g of crude isoflavone derivatives (isoflavone derivatives content: 70%) obtained by an extraction from soybeans with hot water, followed by purification of the extract using a synthetic absorbent, was added to the paste, and further kneading was conducted for 2 hours. Thereafter, the paste was dried under reduced pressure, to yield 11.6 g of powder. The clathrate with β-cyclodextrin thus obtained was evaluated for bitterness, astringency, and roughness by a panel of ten.

EXAMPLE 8

Clathrate of Crude Isoflavone Derivatives with γ-cyclodextrin

The similar process as described in Example 7 was carried out except that γ-cyclodextrin was used instead of β-cyclodextrin to obtain γ-cyclodextrin clathrate. The resulting γ-cyclodextrin clathrate was similarly evaluated by a panel of ten for bitterness, astringency, and roughness.

COMPARATIVE EXAMPLE 4

Clathrate of Crude Isoflavone Derivatives with α-cyclodextrin

The similar process as described in Example 7 was carried out except that α-cyclodextrin was used instead of β-cyclodextrin to obtain α-cyclodextrin clathrate. The resulting α-cyclodextrin clathrate was similarly evaluated by a panel of ten for bitterness, astringency, and roughness.

COMPARATIVE EXAMPLE 5

Crude Isoflavone Derivatives

The crude isoflavone derivatives described in Example 7 was evaluated by a panel of ten for bitterness, astringency, and roughness.

The evaluation referred to in the Example 7 through Comparative Example 5 are shown in the Table 7 below.

TABLE 7

|  | Clathrate | Bitterness | Astringency | Roughness |
|---|---|---|---|---|
| Example 7 | β-cyclodextrin | – | – | – |
| Example 8 | γ-cyclodextrin | + | + | + |
| Comparative Example 4 | α-cyclodextrin | +++ | +++ | +++ |
| Comparative Example 5 | – | ++++ | ++++ | ++++ |

–: none
+: slight
+++: strong
++++: very strong

As shown in Table 7, it is demonstrated that bitterness, astringency, and roughness of the crude isoflavone derivatives can be suppressed through clathration with β-cyclodextrin or γ-cyclodextrin. Especially, when the isoflavone derivatives are clathrated with β-cyclodextrin, the bitterness, the astringency, and the roughness was suppressed considerably. These results are similar to the above-described results in Examples 2 and 3, and Comparative EXAMPLES 1 and 2.

EXAMPLE 9

Jelly Containing Cyclodextrin Clathrate of Crude Isoflavone Derivatives

To 150 ml of water, 360 mg of the clathrate of the crude isoflavone derivatives with β-cyclodextrin obtained in accordance with Example 7 was dissolved. Then, 50 g of fruit juice and granulated sugar were added to the solution. After 2.5 g of agar was added, the mixture was heated to 90° C. with thorough stirring to melt the agar. The heated solution was poured into 50 ml cups made of plastic, and cooled to 5°–10° C. to harden. Thus, a jelly containing crude isoflavone derivatives were prepared.

The jelly was evaluated for bitterness, astringency, and roughness by a panel of ten. The results of the evaluation are shown in Table 8. The jelly made in such a manner was not bitter, astringent, and rough. Moreover, the jelly was very tasty, and had a clear appearance, without any precipitate.

COMPARATIVE EXAMPLE 6

Jelly Containing Crude Isoflavone Derivatives

A process similar to Example 9 was performed except that 60 mg of the crude isoflavone derivatives described in Comparative Example 5 were used instead of the β-cyclodextrin clathrate to prepare jelly containing the isoflavone derivatives. The resulting jelly was evaluated by a panel of ten for bitterness, astringency, and roughness. The results are shown in Table 8.

TABLE 8

|  | Clathrate | Bitterness | Astringency | Roughness |
|---|---|---|---|---|
| Example 9 | β-cyclodextrin | – | – | – |
| Comparative Example 6 | – | ++++ | ++++ | ++++ |

–: none
+++: strong
++++: very strong

It is apparent from Table 8 that the jelly containing the crude isoflavone derivatives which were not clathrated with β-cyclodextrin were bitter, astringent, and rough. On the other hand, the jelly containing the crude isoflavone derivatives clathrated with β-cyclodextrin was not bitter, astringent, and rough. Additionally, no precipitate could be found in the jelly of Example 9 while some precipitate could be found in the jelly of Comparative Example 6. Therefore, solubility of the crude isoflavone derivatives also are improved through clathration with the cyclodextrins.

According to the present invention, water solubility of isoflavone derivatives can be improved, and suppression of bitterness and astringency can be achieved, through clathrating the isoflavone derivatives with cyclodextrins.

In accordance with the present invention, the isoflavone derivatives therefore can be used in edible compositions. Namely, edible compositions containing the isoflavone derivatives having higher water solubility are prepared without undesirable taste.

Accordingly, the present invention can facilitate the oral ingestion and body absorption of isoflavone derivatives. Thus, the effects of the isoflavone derivatives can be sufficiently exerted in the human body, leading to a contribution to humans in maintaining and promoting healthy conditions.

What is claimed is:

1. A clathrated compound comprising:
    (a) an isoflavone derivative selected from the group consisting of daidzein, genistein, glycitein, genistin, glycitin, 6"-O-malonyldaidzin, 6"-O-malonylgenistin, 6"-O-malonylglycitin, 6"-O-acetyldaidzin, 6"-O-acetylgenistin, 6"-O-acetylglycitin, 6"-O-succinyldaidzin, 6"-O-succinylgenistin, 6"-O-succinylglycitin, and mixtures thereof, and
    (b) a cyclodextrin selected from the group consisting of a β-cyclodextrin, a γ-cyclodextrin, and mixtures thereof, wherein the compound has less bitterness, astringency, and roughness than a corresponding nonclathrated isoflavone derivative when orally administered.

2. An edible composition comprising a clathrated compound of claim 1.

3. A clathrated compound comprising:
    (a) an isoflavone derivative selected from the group consisting of daidzein, genistein, glycitein, genistin, glycitin, 6"-O-malonyldaidzin, 6"-O-malonylgenistin, 6"-malonylglycitin, 6"-O-acetyldaidzin, 6"-O-acetylgenistin, 6"-O-acetylglycitin, 6"-O- succinyldaidzin, 6"-O-succinylgenistin, 6"-O-succinylglycitin, and mixtures thereof; and (b) a cyclodextrin selected from the group consisting of β-cyclodextrin, a γ-cyclodextrin, and mixtures thereof, wherein the compound is prepared by clathrating the cyclodextrin and the isoflavone derivative in a weight ratio of cyclodextrin to isoflavone derivative of 0.1:1 to 50:1, and wherein the compound has less bitterness, astringency, and roughness than a corresponding nonclathrated isoflavone derivative when orally administered.

* * * * *

UNITED STATES PATENT AND TRADEMARK OFFICE
CERTIFICATE OF CORRECTION

PATENT NO. : 5,847,108
DATED : December 8, 1998
INVENTOR(S) : Satomi Kanaoka et al.

It is certified that error appears in the above-identified patent and that said Letters Patent is hereby corrected as shown below:

Column 1, line 29, "Epidemio-logical" should be --Epidemiological--

Column 8, line 32, "isoflavone flavone derivatives" should be --isoflavone derivatives--

Column 8, Table 5, column headed "Roughness", Rows 5, 8, & 11, "+" should be -- - --

Column 9, Table 5, column headed "Roughness", Rows 5, 8, & 11, "+" should be -- - --

Column 9, Table 5, column headed "Roughness", Rows 14, 17, 20, 23, 26, & 29, "+" should be -- - --

Column 11, Table 7, column headed "Roughness", Row 2, "+" should be -- - --

Signed and Sealed this

Twenty-eighth Day of March, 2000

Attest:

Q. TODD DICKINSON

*Attesting Officer*  *Commissioner of Patents and Trademarks*